United States Patent [19]

Kenney et al.

[11] Patent Number: 4,861,488

[45] Date of Patent: Aug. 29, 1989

[54] AUTOMATIC CHROMATOGRAPHY PROCESS

[75] Inventors: Andrew C. Kenney, Windsor; Philip W. Thompson, Burnham; John L. Harris, Slough, all of England

[73] Assignee: Oros Systems Limited, England

[21] Appl. No.: 248,789

[22] Filed: Sep. 23, 1988

Related U.S. Application Data

[62] Division of Ser. No. 117,014, Nov. 4, 1988, Pat. No. 4,802,981.

[51] Int. Cl.⁴ ............................................. B01D 15/08
[52] U.S. Cl. ....................................... 210/656; 55/67; 73/61.1 C
[58] Field of Search ...................... 210/656, 659, 198.2; 55/67, 386; 73/61.1 C; 422/70; 530/413, 417

[56] References Cited

U.S. PATENT DOCUMENTS

| | | | |
|---|---|---|---|
| 4,237,422 | 12/1980 | Lenhardt | 210/656 |
| 4,450,082 | 5/1984 | Tanouchi | 210/656 |
| 4,468,330 | 8/1984 | Kamiyama | 210/656 |
| 4,476,713 | 10/1984 | Alfredson | 210/656 |
| 4,544,485 | 10/1985 | Pinkerton | 210/656 |
| 4,579,663 | 4/1986 | Poile | 210/656 |
| 4,614,620 | 9/1986 | Konai | 210/656 |
| 4,629,705 | 12/1986 | Cortes | 210/656 |
| 4,694,682 | 9/1987 | Heikkila | 210/656 |
| 4,719,017 | 1/1988 | Uchino | 210/656 |

Primary Examiner—Ernest G. Therkorn

Attorney, Agent, or Firm—Ostrolenk, Faber, Gerb & Soffen

[57] ABSTRACT

Automatic chromatography apparatus comprises a column packed with adsorbent or attractant material;

means for supplying an elutant solution to the column;

loading means for loading controlled quantitites of a material into the column, the material containing a substance to be eluted;

automatic control means which control the loading means so as to load the column with a first charge of the material and subsequently to load the column with a second charge of the material, the first charge being sufficiently small to ensure that the capacity of the column is not exceeded and the second charge being sufficiently large to ensure that the capacity of the column is exceeded;

first monitoring means for monitoring and controlling flow rate to provide accurate flow information to enable peak area integration;

second monitoring means which monitor the peaks of elution of the substance from the column resulting from the first and second charges of material;

processing means connected to the monitoring means and arranged to integrate the elution peak with respect to the first charge of material so as to derive the concentration of the substance in the material, and to determine from the peak of elution of the substance from the column resulting from the second charge of material the maximum practical capacity of the column for the said substance.

9 Claims, 2 Drawing Sheets

AUTOMATIC CHROMATOGRAPHY PROCESS

This is a division of application Ser. No. 117,014, filed Nov. 4, 1988, now U.S. Pat. No. 4,802,981.

This invention relates to an automated system for chromatography, particularly adsorption chromatography, and in particular adsorption chromatography of monoclonal antibodies.

In the preparation of microbiological and cell culture derived products such as monoclonal antibodies or fragments thereof, the main problem is the separation of the required material from raw materials and by-products and also from the preparation medium. It is frequently the case that the concentration of the required product in the preparation medium is in fact very low, so that the product has to be won from large volumes of culture liquor.

A convenient method for capturing and isolating materials such as monoclonal antibodies and fragments thereof comprises chromatography, particularly affinity chromatography, in which the meduim is contacted with an adsorbent or otherwise attractant material in a column so that the required product is bound, and the column is subsequently eluted with a suitable medium to cause the product to become selectively unbound.

Practical problems arise in running column chromatography of this type, especially on a preparative, as opposed to an investigative, scale. Often, the affinity of the product for the column packing is unknown, especially if the product is new. Secondly, the concentration of the desired product in the medium may not be known with any degree of accuracy, and thirdly the degree of purity of the medium may not be known. For example, the preparation of a monoclonal antibody supply may be contaminated with rogue polyclonal products. There is thus always a considerable degree of investigation and calibration to be done before routine chromatography can be carried out. Such investigative work can be time consuming and troublesome and can also lead to wastage of highly valuable product. There is thus a need for an automated system which solves these problems.

This invention provides a novel application of expert software control to a chromatography system and also to particular combinations of apparatus of use in this process.

According to a first aspect of the present invention there is provided automatic chromatography apparatus comprising:

a column packed with adsorbent or attractant material;

means for supplying an elutant solution to the column;

loading means for loading controlled quantities of a material into the column, the material containing a substance to be eluted;

automatic control means which control the loading means so as to load the column with a first charge of the material and subsequently to load the column with a second charge of the material, the first charge being sufficiently small to ensure that the capacity of the column is not exceeded and the second charge being sufficiently large to ensure that the capacity of the column is exceeded;

first monitoring means for monitoring and controlling flow rate to provide accurate flow information to enable peak area integration;

second monitoring means which monitor the peaks of elution of the substance from the column resulting from the first and second charges of material;

processing means connected to the monitoring means and arranged to integrate the elution peak with respect to the first charge of material so as to derive the concentration of the substance in the material, and to determine from the peak of elution of the substance from the column resulting from the second charge of material the maximum practical capacity of the column for the said substance; and, optionally, means for providing a controlled change in time in a chemical parameter of the elutant supplied to the column under control of the control means thereby enabling the processing means to determine from elution peaks monitored by the monitoring means the optimum value for said parameter for elution of the said substance and whether or not other similar substances are being eluted from the column. The parameter can be, for example, the pH, the ionic strength or the chemical composition, e.g. the presence of a certain quantity of a chaotropic agent such as urea, guanidine etc.

According to a second aspect of the present invention there is provided a method of automatic chromatography characterisation comprising the steps of: automatically;

loading onto a column packed with adsorbent or attractant material a relatively small sample containing a substance to be eluted, the relatively small sample being sufficiently small so as to ensure that the adsorption capacity of the column is not exceeded;

eluting the substance from the column to obtain an elution peak;

integrating the elution peak with respect to the relatively small sample so as to derive the concentration of the substance in the sample;

loading the column with a relatively large sample containing the substance, the relatively large sample being sufficiently large to ensure that the capacity of the column is exceeded;

calculating the maximum practical capacity of the column; and, optionally providing a controlled change in time in a chemical parameter of the elutant supplied to the column to determine the optimum value at which the substance can be eluted.

The apparatus and method are suitable for chromatographic separation generally, but are particularly suitable for affinity chromatography especially immunological affinity chromatography needed for the separation of monoclonal antibodies. Thus, the column packing can be any suitable adsorbent or otherwise attractant material, but for immunological purposes a substance which can bind to an antibody or a fraction thereof by means of specific affinity is most suitable. A particularly desirable material comprises an inert packing to which is bound an immunological material such as Protein A.

The packing generally comprises a rigid or semi-rigid inert support material, either porous or nonporous, of which many are known and produced commercially, for example Sepharose and other agarose-based materials, silica and derivatives and other synthetic organic polymers and copolymers. Preferably, a 60 micron porous bead (pore size 3500 nm) composed of hydroxyethylmethacrylate to which protein A (obtained either naturally or by means of genetic manipulation) is convalently attached using a chemical means of which many are known but preferably by means of divinylsulphone.

The amount of protein A may be attached to the support material is, in practice, limited only by the chemical means of attachment, but preferably 2.5 to 3.5 mg of protein A is attached per ml of support material.

One of the problems of continuous chromatography of this type is that after a while the column becomes overloaded with impurities and by-products so that the capacity for the required product and the sharpness of the elution peak for that product gradually decrease. Under such circumstances, it is usually necessary for some kind of cleaning cycle to be operated before the column can be operated at its optimum efficiency. It is therefore desirable that the apparatus should be provided with means for determining when such an operation becomes necessary.

According to a further aspect of the present invention there is provided apparatus for controlling the efficiency of operation of a chromatography column, comprising:

monitoring means which monitor the shape and magnitude of the elution peak of the substance on the column;

memory means for storing at least one reference and details of one or more corrective actions which may counteract deterioration of the said efficiency of operation;

comparator means which compare output from the monitoring means with the said reference;

processing means which apply output from the comparator means to select a stored corrective action; and control means which automatically execute the selected corrective action.

According to a still further aspect of the present invention, there is provided a method of controlling the efficiency of operation of a chromatography column, comprising the steps of:

monitoring the continuing performance of the column by automatic elution peak analysis, said peak analysis including the comparison of peak shape and magnitude with at least one prestored reference, the analysis further including identifying from a plurality of prestored options the most probable corrective action to counteract deterioration of the said efficiency of operation; and automatic execution of the identified corrective action.

The system may select corrective actions from a choice of several but also may try choices in a sequence, moving from one to another as the benefit of the first is exhausted.

Preferably, peak shape analysis comprises determining the degree of asymmetry of the peak.

Beneficially, two references are prestored, one of the references being varied in accordance with the efficiency of the column itself and the other of the references representing the minimum acceptable efficiency of the column.

A more detailed description of the apparatus and its use follows.

A typical characterisation sequence for use with a monoclonal antibody on a protein A column is as follows:

The objective of the characterisation cycle is to obtain certain parameters for an unknown antibody which enable the instrument to set itself up automatically to purify the antibody with maximum efficiency.

The parameters obtained are as follows:
1. The capacity of the column for the antibody.
2. The concentration of antibody in the crude feedstock.
3. The pH at which the antibody can be eluted from the column.
4. The number of resolvable peaks in the chromatogram.

These parameters are stored by the software to be used subsequently to control the operation of the purification runs. They are needed for the following reasons:

1. In order to load an amount of antibody onto the column which is as high as possible without losing part of that antibody in the unbound protein fraction, it is necessary to know the capacity of the column for that particular antibody. This capacity will be different for different antibodies and so the capacity must be established for each new antibody of interest.

2. Once the capacity is known, the volume of feedstock to load for each purification cycle can only be calculated from the concentration of antibody in the feedstock. This is often not known accurately beforehand.

3. Antibody is eluted from the column by lowering the pH of the solution passing through the column. Different antibodies will be eluted at different pH values. Whilst it would be possible to elute all antibodies at, say, pH 3.0, many antibodies are not stable at low pH and so it is important to elute at as high a pH as possible. This must be determined experimentally for each antibody of interest.

4. A clonal hybridoma culture should only produce a single monoclonal antibody. However sometimes by accident cell cultures are used to produce antibody that are di-, tri- or polyclonal and so more than one antibody may be found in the culture fluid. Furthermore, cells may be grown in animal serum that contains antibody from another species, or in mouse ascites which contains normal polyclonal mouse antibodies. In each of these cases it is possible that on elution of the antibody from protein A, more than one peak of antibody may be obtained. By running a pH gradient during the characterisation sequence the instrument may detect these additional components and prompt the operator to analyse each component and tell the computer which of the peaks is of interest and should be collected during the purification runs. Where the characterisation experiment gradient only achieves partial resolution of peaks, a second, shallower gradient may be run on a repeat cycle to attempt a better resolution.

These parameters may be obtained automatically by the instrument as follows:

When a new antibody is presented to the machine, the operator causes it to perform the characterisation sequence by making an entry at the keyboard.

The machine is also told the source of the antibody (e.g. ascites, cell culture or concentrated cell culture) and the operator's estimate of the antibody concentration, if possible. From this information the software calculates approximately how much feedstock to load in order to achieve 5–15% saturation of the column. Under this condition all of the applied antibody will be retained by the column and, on elution, the peak integral may be used to calculate accurately the total antibody concentration. The elution in this automatic experiment is done at pH 3 to obtain a single eluted peak.

Next the instrument loads the column with an amount of antibody equivalent to more than an estimate of the saturation amount. The estimate is made on the basis of experience of typical saturation values for different types of antibody which have been previously determined by experiment and stored in the computer. During the loading of this material, the unbound protein stream is returned to the feedstock vessel to avoid loss of antibody in the waste stream. The volume returned in this way is recorded. Alternatively this stream may be collected in a separate vessel. The bound antibody is then eluted from the column, this time using a linear pH gradient from 8.8 down to 2.0. The integral values of the total number of peaks of eluted antibody obtained is used to determine the saturation capacity of the column. In cases where more than one peak is obtained, the operator is prompted to decide which of the peaks is/are collected. This peak is then used to determine the saturation capacity. Where the unbound protein stream was returned to the feedstock vessel, the total antibody eluted from the column is used to perform a calculation to take account of the now diluted feedstock and a revised concentration for the remaining antibody is obtained.

The chromatogram obtained is used by the software to determine the appropriate pH for elution. This is done by relating the protein concentration measurements to the pH measurements and selecting a pH which is equivalent to the point at, say, 75% of the peak width.

The characterisation sequence described above derives the antibody concentration and column capacity for each new antibody.

These values can be in error to an extent where the performance of the instrument would be compromised and so a routine is performed during each separation which checks the actual yield (peak integral) against expected values obtained during characterization and takes appropriate action if significant deviations are detected. This routine can also spot the onset of column fouling by detecting the reduction in yield that often accompanies fouling.

DESCRIPTION OF THE PREFERRED EMBODIMENTS

Figure 1:
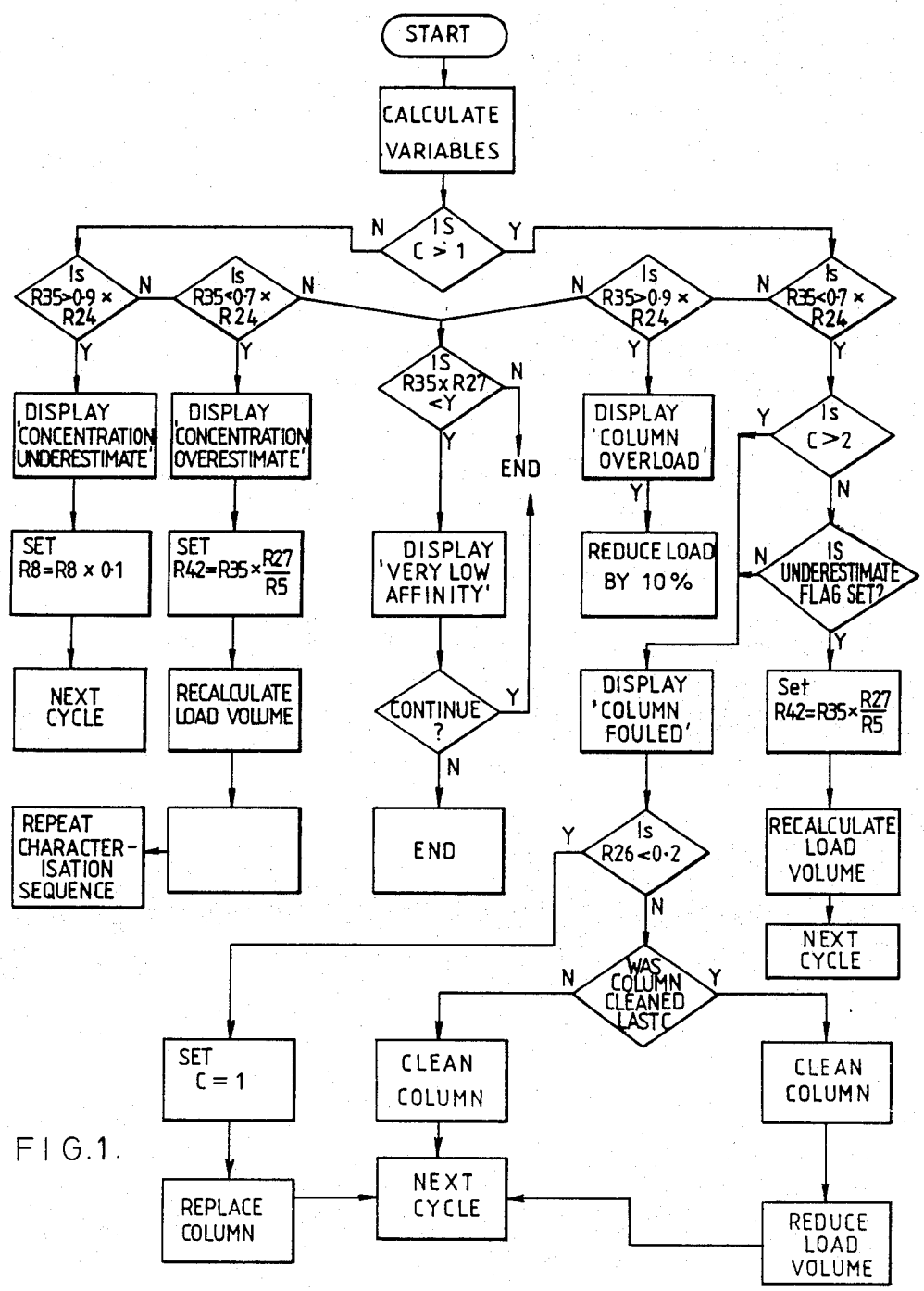
FIG. 1 shows a flow sheet for determining the column capacity.

The flow sheet in FIG. 1 illustrates this rather complex routine and the variables have the following meaning:

R35 = peak integral from last cycle
R24 = expected peak integral from characterisation cycle
C = cycle number
R27 = conversion factor to generate mass from peak integral
R5 = volume of feed to load
R42 = corrected feed concentration
R8 = column capacity

FIRST CYCLE (C=1)

The peak integral obtained is compared with 70% and 90% of the expected peak integral. A value below 70% indicates that the original concentration estimate was too high and so on the basis that all of the antibody on this cycle was captured and eluted, the actual concentration may be estimated from this eluted mass divided by the volume of feed that was applied. Since too high a concentration estimate would have lead to the determination of a capacity that was possibly too low, the instrument then performs the characterisation cycle again using the revised concentration estimate.

A value for the peak integral above 90% of expectation indicates that the concentration was probably underestimated at the start and so the load volume for the next cycle is set to 10% of the previous value. On subsequent cycles the load volume will be increased until the obtained peak integral falls in the 70-90% range.

SECOND CYCLE (C=2)

The range comparison is made again this time from the second cycle peak integral. Integrals falling within the range are ignored and the next cycle is performed without adjustment. Integral values below 70% will indicate that the column has possibly become fouled since the first cycle (concentration overestimate is not possible this time since it would have been detected and corrected on the first cycle). If on the first cycle an underestimate was diagnosed then the concentration is recalculated from the eluted mass and the volume of feed applied. Using this corrected concentration, the feed volume is then adjusted and the next cycle performed. This strategy will work because if an underestimate was diagnosed on the first cycle, the feed volume will have been set to 10% of the original feed value (see above). Consequently, one would have expected to obtain a low peak integral on the second cycle in order to recalculate the feed concentration accurately.

If a concentration underestimate was not diagnosed on the first cycle, then the yield obtained is tested to determine whether it is below a preset lower limit. If it is, then the run is aborted and a column replacement is recommended. If the yield is above the preset lower limit then the software determines that a cleaning cycle should be performed before the next cycle.

If the second cycle peak integral is above 90% of the expected value then an overload is assumed and the load volume is reduced by 10%. This protects against a loss of antibody in the unbound protein fraction because the capacity was exceeded.

SUBSEQUENT CYCLES (C>2)

As before, the integral obtained is compared with the range 70-90%. Integrals falling below 70% indicate column fouling and this leads to the same analysis of yield as for the second cycle case above. However, if the yield is below the preset lower limit then the run may be aborted and a column replacement is recommended. If the yield is above this preset lower limit, then the software checks to seewhether a cleaning cycle was performed before the last cycle. It it was, then another cleaning is performed before the next cycle but the loaded volume is reduced to an amount determined from the actual yield of the most recent cycle. This takes account of the gradual loss of column capacity as fouling increases cycle by cycle. If no cleaning took place, then the column is cleaned and the next cycle runs without a reduction in load volume, since the cleaning may well restore the capacity.

For peak integrals above 90%, the same load reduction sequence is triggered as for the same case for the second cycle above.

The peak analysis routines are as follows, in a preferred embodiment:

1. Peak Shape.

The peak shape analysis is performed by the control computer after every separation run on the instrument.

The objective is to detect on-line any deterioration in performance during the run and then to take action to correct it.

The first step is to perform a calculation on the peak and determine a parameter (skewness) which represents the extent to which the eluted peak diverges from a symmetric distribution. The skewness factor obtained is then compared with a preset level of acceptable skewness and if a value in excess of this acceptable level is found, then corrective action is taken. The acceptable level of skewness (P) is a variable resident in the software which is set from experimental determination of the best peak shape obtainable with the system. A new column has a P value which is set on installation of the column. As the performance of the column deteriorates, the P value is adjusted so that at any time it represents the best peak shape obtainable with the particular column in place.

There is further constant (P') which represents an extreme value for the skewness. At the point where the determined skewness reaches P', it is judged that the column in place is no longer servicable and should be replaced.

Once the skewness value has been determined, the software proceeds to work through a decision tree which enables it to take the appropriate corrective action.

Two basic factors can cause the eluted peak shape to deteriorate from the expected shape.

The first of these is elution pH. If the characterisation sequence determines an elution pH which in practice turns out to be too high, then antibody will not be eluted from the column with the maximum efficiency and so the peak obtained will tend to broaden and an extended tail to the peak may be obtained. The second factor is column fouling. The crude feedstocks that are used with the instrument may contain lipid and denatured protein which will tend to interact with the column in a non-specific fashion and may not be eluted during normal cycling. Eventually the build up of these materials will give rise to uneven flow through the column and consequently the shape of the eluted peak will deteriorate. This may be corrected wholly or in part by cleaning the column with appropriate solutions.

Before any production run the column will have been cleaned and so if poor peak shape is detected at the outset it most likely to be a pH problem and so initially the software adjusts the elution pH downward by 0.5. However, if during the characterization experiments the apparatus detected a second unwanted peak within 1 pH unit of the peak of interest, pH adjustment would not be attempted as this might lead to inadequate resolution of the two components. The next separation cycle is then run and the skewness factor determined. If there has been an improvement over the previous cycle but the skewness is still above the preset value 'P' then the pH is again decremented by 0.5 and another cycle is performed. If the skewness is now below P then the next cycle is performed without further adjustment.

Once the potential to improve the shape using pH has been exhausted or the shape improvement has resulted in a skewness of less than P, then a flag is set in software to indicate that no further pH adjustment should be attempted.

Where a pH adjustment is made and fails to improve the peak shape on the next production cycle, then the pH is restored by 0.5 and a cleaning sequence is performed before the next production cycle.

If a poor peak shape fails to be improved by pH adjustment or is improved up to a point but still has a skewness greater than P, then a cleaning cycle is performed before the subsequent production cycle.

The skewness obtained from the eluted peak from a cycle performed after the column has been cleaning is checked against P', the maximum allowable skewness. If this value is exceeded then the instrument warns the operator that the column is now performing below specification and recommends replacement. Whether P' is exceeded or not, the software resets P to the skewness determined on the cycle following a clean since this is now likely to be the best possible peak shape obtainable with the column in place.

The new value of P is retained in software for use on subsequent runs since this variable is a characteristic of the column installed on the machine. When the column is replaced, P is reset to the original value.

DETERMINATION OF SKEWNESS

Mean $(x) = $ (sum from $i=1$ to n of $x_i * y_i$) / (sum from $i=1$ to n of $y_i$)

Variance $(s^2) = $ (sum from $i=1$ to n of $y_i (x_i - x)^2$) / (sum from $i=1$ to n of $y_i$)

Standard Deviation $= S$

Third Moment $(m3) = $ (sum from $i=1$ to n of $y_i (x_i - x)^3$) / (sum from $i=1$ to n of $y_i$)

Coefficient of Skewness $= m3/S^3$ where, $Y_i = $ protein concentration value at a point, $X_i$ along the eluted volume axis of the peak; and $i = $ the number of the coordinate out of a total of n coordinates which define the peak.

The coefficient of skewness will be 0 for a perfectly symmetrical peak and will have increasing positive or negative values reflecting the extent to which the leading or trailing edges of the peak deviate from normality.

Under the situation described here only trailing edge deviations will be observed and hence the extent of the positive value for the skewness can be used as a measure of the extent to which the eluted peak "tails".

This mathematics is a well known statistical manipulation and is included for information only.

Figure 2:
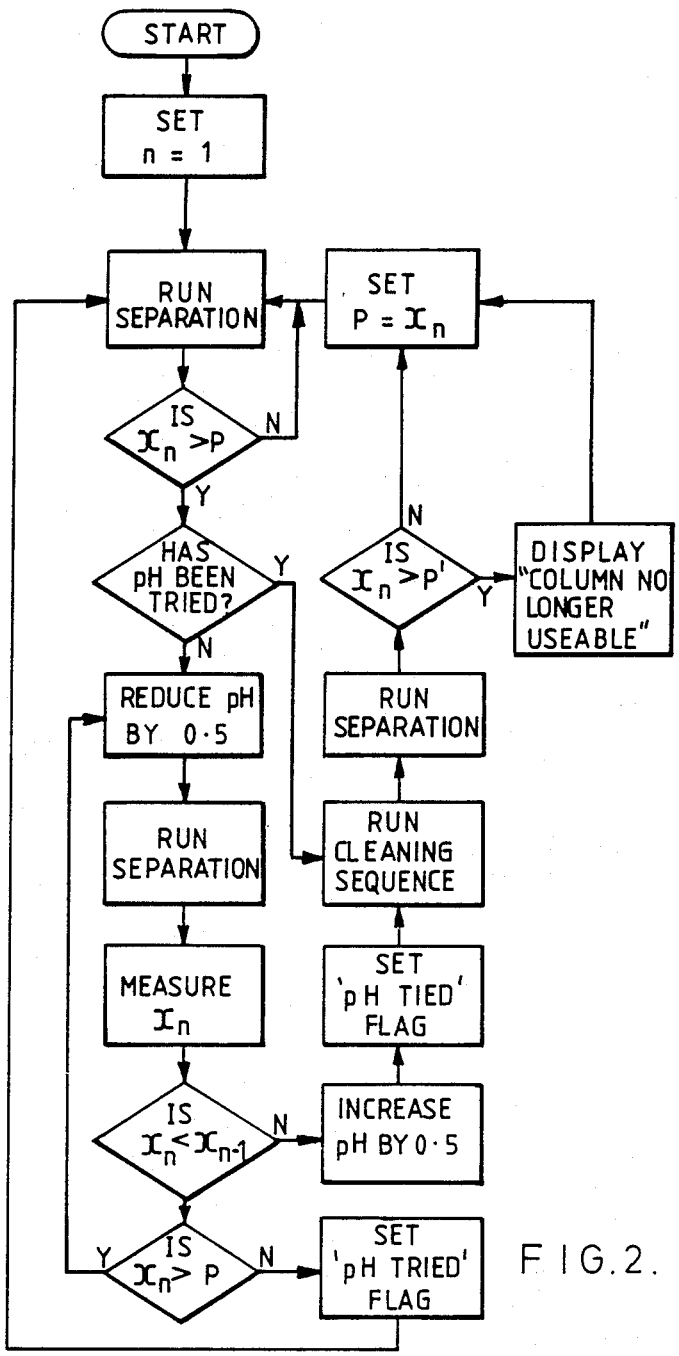
FIG. 2 shows a flow sheet for determining column deterioration.

The sequence of steps is illustrated in FIG. 2.

In the above procedure no account is taken of the nature of the deterioration in the peak shape. Only the extent of deviation from a symmetrical peak is considered.

By means of the following procedure it is possible to separate shape changes leading to wider but symmetrical peaks from wider but asymmetrical peaks. This is of use to the control system because wide symmetrical peaks are usually the result of column fouling whilst wide asymmetrical peaks are usually the result of too high an elution pH.

This procedure works as follows:

After the peak has been eluted from the column, two measurements are made. Firstly the width of the peak is measured between set thresholds of protein concentration. Secondly, the position of the peak maximum is measured and the width of the leading edge of the peak is determined.

If the peak width is less than a preset value of acceptability (w') then no action is taken.

If the width exceeds this preset value then the width of the leading edge is also compared with a preset value of acceptability (l'). In this case if this leading edge width is exceeded then a cleaning cycle is performed, since this indicates that the peak is probably symmetrical but of excessive width.

If the leading edge width is within the limit of l', then the instrument decreases the elution pH by 0.5, since this indicates that, despite the excessive width of the peak overall, the leading edge is normal.

In deciding whether to adjust the pH downward, the software first checks from the characterisation data that there is not a second peak set to elute at a lower pH. If such a second peak does exist and it is within a pH unit of the peak of interest, then a reduction in elution pH would cause co-elution of the two.

It will be appreciated that these two strategies for managing changes in the shape and width of eluted peaks can be combined.

The apparatus according to the present invention may incorporate a number of optional features to aid effective use.

One such feature is an automatic arrangement for changing to an alternative filter. The inlet stream to the chromatography column should, desirably, pass through a filter to exclude undissolved residues. In the course of time such a filter becomes overloaded and ceases to be efficient. A simple arrangement for overcoming this problem is to have two filters connected in parallel, with the flow of liquid controlled by a toggle valve. Upstream of the toggle valve the pipeline is provided with a pressure sensor connected to operating means serving to actuate the toggle valve. Thus, in operation, liquid passes the pressure sensor and leaves the toggle valve to pass through one of the filters. After a certain time, the back pressure in the system builds to an undesirable level. The pressure sensor and actuating means are calibrated to operate when the pressure reaches this predetermined value and the toggle valve is switched so that the liquid flow passes the second filter. The first filter can then be removed and cleaned or replaced.

Another useful feature for the apparatus according to this invention is the provision of sensing means, for example small infra-red detectors, to monitor liquid levels in the storage vessels to which product solutions etc. are delivered. The sensing means can be arranged to detect whether the storage vessel is full or empty. In a particularly preferred embodiment, the apparatus is provided with means to signal the absence of the vessel, for example a spring-loaded interrupter arranged to interrupt the infra-red beam if the storage vessel is removed. The sensing means can be arranged to cooperate with control means serving to control filling and washing cycles etc.

In a further preferred embodiment, a device to eliminate gas bubbles from the feed stream to the column comprises 2 level sensing devices mounted one above the other in a cyclindrical chamber which is also provided with ports for the entry and exit of the liquid flow at the base and a further port at the top of the chamber above the level sensing devices which is connected to a valve. This is under the control of the computer and when opened connects the inside of the chamber to the atmosphere. Bubbles of gas entering the chamber rise up before they can be removed in the exit stream and replace the liquid which initially fills the chamber. The upper of the 2 level sensing devices detects when this collected gas exceeds a certain volume and as a consequence the control computer opens the vent valve until the gas is replaced in the chamber by liquid from the inlet stream. If a large quantity of gas enters the chamber or if the upper level sensing device fails then the second, lower level sensor will detect an abnormally large quantity of gas in the chamber and as a consequence the computer will divert the flow from passing through the column in order to protect it from damage caused by entry of gas, as well as opening the vent valve.

In another preferred embodiment, the provision of a gradually changing pH in the elutant solution over a period of time can be achieved by arranging two buffered solutions to flow in parallel to a toggle valve connected to a single conduit leading to the column. The toggle valve is arranged so that for part of the cycle one of the buffer solutions is passed to the conduit and for the remainder of the cycle the other buffer solution is passed to the conduit. Control means can be provided to adjust the ratio between these times on a gradually changing basis, so that the pH of the emerging elutant gradually changes. Throughout the operation, the toggle valve "toggles", i.e. constantly switches from one supply to the other and back again.

Typical buffer solutions for this purpose are a phosphate buffer at pH 8.8 and a citrate buffer at pH 2.0. For preferance, the conduit is connected to the column via auxiliary mixing means, such as a small reservoir, optionally fitted with baffles. To be effective, the reservoir should have a volume equal to the output of the toggle valve over a number of toggle cycles, so that the alternate streams of buffer have a chance to mix and stabilise before passing to the column. In this way an effectively linear transition of pH can be achieved very simply.

We claim:

1. A method of automatic chromatography characterization comprising the automatic steps of;
  loading onto a column packed with adsorbent or attractant material a relatively small sample containing a substance to be eluted, the relatively small sample being sufficiently small so as to ensure that the adsorption capacity of the column is not exceeded;
  eluting the substance from the column to obtain an elution peak;
  integrating the elution peak with respect to the relatively small sample so as to derive the concentration of the substance in the sample;
  loading the column with a relatively large sample containing the substance, the relatively large sample being sufficiently large to ensure that the capacity of the column is exceeded; and
  calculating the maximum practical capacity of the column.

2. The method of claim 1 in which a controlled change in time in a chemical parameter of the eluent supplied to column is provided to determine the optimum value at which the substance can be eluted.

3. The method of claim 2 in which the including controlled change in time in a chemical parameter is selected from the group consisting of pH, ionic strength and chemical composition.

4. The method of claim 2, wherein the said adsorbent or attractant material comprises an inert packing to which is bound an immunological material.

5. The method of claim 4, wherein the said immunological material comprises protein A.

6. The method of claim 3 which includes providing a controlled change in time in a chemical parameter of the eluent supplied to the column to determine the optimum value at which the substance can be eluted.

7. The method of claim 6 in which the controlled change in time in a chemical parameter is selected from the group consisting of pH, ionic strength and chemical composition.

8. The method of claim 7 wherein the said immunological material comprises protein A.

9. The method of claim 1 which includes the steps of: monitoring the continuing performance of the column by automatic elution peak analysis, said peak analysis including the comparison of peak shaped magnitude with at least one prestored reference, the analysis further including identifying from a plurality of prestored options the most probable corrective action to counteract deterioration of the said efficiency of operation; and automatic execution of the identified corrective action.

* * * * *